US00PP37084P2

(12) United States Plant Patent
Lee

(10) Patent No.: US PP37,084 P2
(45) Date of Patent: Nov. 4, 2025

(54) ***LEUCOTHOE* PLANT NAMED 'BLLE01'**

(50) Latin Name: *Leucothoe axillaris*
Varietal Denomination: BLLE01

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 18/955,736

(22) Filed: Nov. 21, 2024

(51) Int. Cl.
*A01H 5/02* (2018.01)
*A01H 6/36* (2018.01)

(52) U.S. Cl.
USPC ..... Plt./226
CPC ..... *A01H 6/36* (2018.05)

(58) Field of Classification Search
USPC ..... Plt./226
CPC ..... A01H 5/02
See application file for complete search history.

*Primary Examiner* — Kent L Bell

(57) ABSTRACT

A new and distinct cultivar of *Leucothoe* plant named 'BLLE01' is disclosed, characterized by bronze red new growth in Spring and with each growth flush. White flowers from the leaf axils which attract pollinators. Plants are compact and spread laterally, reaching about 3 to 4 feet wide and 2.5 to 3 feet in height. The new cultivar is a *Leucothoe*, suitable for ornamental garden purposes.

1 Drawing Sheet

Latin name of the genus and species: *Leucothoe axillaris*.
Variety denomination: 'BLLE01'.

BACKGROUND OF THE INVENTION

The new cultivar, hereinafter referred to as 'BLLE01', was discovered as part of a breeding program at a commercial nursery in Independence, LA. The intention of the breeding program was to develop new *Leucothoe* varieties for commercial ornamental purposes. This new discovery is the result of an open-pollination of various unnamed, unpatented *Leucothoe axillaris* varieties conducted by the inventor during 2016. Plants of several unnamed varieties of *Leucothoe axillaris* were planted in close proximity in a field to allow open-pollination between these parent varieties. Seeds were bulk collected.

'BLLE01' was selected as a seedling in the Fall of 2018 at the same commercial nursery in Independence, LA. After identifying the new variety as a potentially interesting selection, the inventor first organized propagation of 'BLLE01' by softwood cuttings at the same commercial nursery during the Fall of 2018. The inventor continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'BLLE01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLLE01'. These characteristics in combination distinguish 'BLLE01' as a new and distinct *Leucothoe* cultivar:

1. Bronze red new growth in Spring and with each growth flush.
2. Compact lateral growth habit, 2.5 to 3 feet in height and 3 to 4 feet in width.
3. White flowers emerge from leaf axils attracts pollinators
4. Bronze red new growth transitions into dark green shiny leaves.
5. Evergreen plant that can be used as a hedge or a specimen plant.
6. Assumed cold hardy to Zone 5 with protection in colder areas.
7. Winter leaf colored bronze.
8. Tolerance of various fungal diseases observed.

COMPARISON TO PARENT VARIETY

The exact parent varieties cannot be identified.

COMMERCIAL COMPARISON

*Leucothoe* 'BLLE01' can be compared to the commercial variety *Leucothoe crenata* 'Little Flames', U.S. Plant Pat. No. 25,246. Plants are similar in most horticultural characteristics; however, plants of the new variety differ in the following:

1. Mature width of 'BLLE01' is about 3 to 4 feet; 'Little Flames' has a mature width of 2 feet.
2. New growth and Fall foliage color of 'BLLE01' is different than that of 'Little Flames'.

BRIEF DESCRIPTION OF THE PHOTOGRAPH

The accompanying photograph illustrates in full color a typical plant of 'BLLE01' grown outdoors in Loxley, AL.

The plant is approximately 1.5 years old, in a 2-gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart 2015 except where general terms of ordinary dictionary significance are used. The following observations and measurements describe 'BLLE01' plants grown outdoors in Loxley, AL. Plants are approximately 2.5 years old, in a 5-gallon nursery container. Measurements and numerical values represent averages of typical plant types.

Botanical classification: *Leucothoe axillaris* 'BLLE01'.

PROPAGATION

Typically by semi-hardwood cuttings in Spring and Summer.

Root Description: Fleshy, moderately dense roots. Colored near RHS Orange-White 159D. New growth of roots colored Greyed-Purple 184D.

PLANT

Growth Habit: Globular evergreen shrub. Low growing.
Height: Approximately 30 cm.
Plant Spread: Approximately 40 cm.
Branching Characteristics: Well branched; about 3 large primary branches at the center of the plant. Each primary branch has 5 to 9 lateral branches. Branches occur at approximately 30° to 90° angles.
Primary Branches:
Length of Primary Branches: Average range 2 to 5 cm, then branching into further laterals.
Diameter of Primary Branches: Average range 11 mm to 22 mm.
Primary Branch Strength: Very strong.
Primary Branch Color: Near RHS Greyed-Orange 176C, streaked with scales colored near Greyed-Purple 183B.
Primary Branch texture: Rough, slightly scaly.
Lateral Branches:
Number of Lateral Branches: Approximately 5 to 9 per primary branch.
Length of Lateral Branches: Average range 10 to 25 cm.
Diameter of Lateral Branches: Average 4 mm 6 mm.
Lateral Branch Strength: Moderately strong.
Lateral Branch Color: Young growth: Green 143C flushed Yellow-Green 144C.
Mature growth: RHS Greyed-Green195A with overlay of Greyed-Purple 183C.
Lateral Branch texture: Glabrous, rough.
Internode length: Average 1.5 to 2.3 cm.
Age of Plant Described: Approximately 2.5 years.

FOLIAGE

Leaf:
*Type*.—Simple.
*Arrangement*.—Alternate.
*Average Length*.—Approximately 4.8 to 5.5 cm.
*Average Width*.—Approximately 2.0 to 2.3 cm.
*Shape of blade*.—Ovate.
*Apex*.—Acute.
*Base*.—Attenuate.
*Attachment*.—Stalked.
*Margin*.—Entire.
*Texture of top surface*.—Glabrous.
*Texture of bottom surface*.—Glabrous.
*Appearance of top surface*.—Moderately glossy.
*Appearance of bottom surface*.—Matte.
*Color*.—Emerging foliage upper side: Yellow-Green 144A flushed Greyed-Orange 163A. Margin Red-Purple 59B. Slight marginal flush near Red-Purple 58C. Emerging foliage under side: Yellow-Green 147D lightly flushed Yellow-Green 151C. Very fine margin Red-Purple 59B. Slight marginal flush near Red-Purple 58C. Young foliage upper side: RHS Yellow-Green 146C flushed 144C. Very fine margin Red-Purple 59B. Mid veins flushed 59B. Young foliage under side: Near RHS Yellow-Green 147D. Very fine margin Red-Purple 59B. Mid veins flushed 59B. Mature foliage upper side: RHS Green 137A. Very fine margin Red-Purple 59B. Mature foliage under side: Near RHS Yellow-Green 146C. Very fine margin Red-Purple 59B. Fall foliage upper side: RHS Green 137A flushed Greyed-Purple 183C. Fall foliage under side: RHS Yellow-Green 146C flushed Greyed-Purple 183D.
*Venation*.—Type: Pinnate. Venation color upper side: Yellow-Green 145A. Venation color under side: Yellow-Green 145A.
*Petiole*.—Average Length: 3 mm Average Width: 1.5 mm Texture: Glabrous. Color: Yellow-Green 145C. Red-Purple 59B at attachment to branch.

FLOWER

Inflorescence: Axillary racemes, 5 to 10 per branch. Flowering begins around early Summer in the Southern United States.
*Length*.—2 to 4 cm.
*Diameter*.—1.4 to 2.2 cm.
*Flowers Per*.—5 to 20.
Flower:
*Shape*.—Urceolate.
*Diameter*.—4 to 6 mm.
*Depth*.—4 to 7 mm.
*Aspect*.—Pendulous.
*Persistence*.—Self-cleaning.
*Lastingness*.—About 3 weeks.
Petals:
*Quantity*.—5.
*Arrangement*.—Whorl. Fused into a bell shape.
*Length*.—4 to 7 mm.
*Width*.—3 to 4 mm.
*Apex*.—Acute.
*Base*.—Fused.
*Margin*.—Entire.
*Texture, upper and lower surfaces*.—Glabrous.
*Color*.—Immature: All surfaces Yellow-Green 150C. Mature: All surfaces White NN155B 8
Peduncle:
*Length*.—2 cm.
*Diameter*.—2 mm.
*Color*.—Near Green 143B.
*Strength*.—Moderate.
*Texture*.—Glabrous.

Pedicel:
*Length*.—2 mm.
*Diameter*.—1 mm.
*Color*.—Near White N155A.
*Strength*.—Moderate.
*Texture*.—Glabrous.

Bud:
*Shape*.—Oblong.
*Length*.—Approximately 2 mm.
*Diameter*.—Approximately 1 mm.
*Color*.—Near RHS Yellow-Green 150D.

Sepals:
*Quantity*.—5.
*Length*.—2 mm.
*Width*.—2 mm.
*Shape*.—Deltate.
*Color*.—Interior and Exterior Surfaces: Near RHS White 155C flushed Green 143C.
*Texture*.—All surfaces glabrous.

Fragrance: Moderate.

REPRODUCTIVE ORGANS

Stamens:
*Number*.—Typically 7. Basifixed.
*Filament Color*.—RHS Green-White 157D.
*Filament Length*.—2 mm.

Anthers:
*Shape*.—Linear.
*Length*.—1 mm.
*Color*.—RHS Greyed-Orange 166C.
*Pollen Amount*.—Not observed.

Pistil:
*Number*.—1.
*Length*.—4 mm.
*Style*.—Length: 2 m. Color: RHS Yellow-Green 144B.
*Stigma*.—Shape: Rounded. Color: RHS Yellow-Green 144B. Ovary Color: RHS Yellow-Green 147A.

OTHER CHARACTERISTICS

Fruits and Seeds: Not observed to date.

Disease and Pest Resistance: The new cultivar was selected in a field in which various unidentified diseases typical of *Leucothoe* were present. The new variety showed tolerance for the various diseases, while other varieties showed susceptibility in the same field. Plants of the new cultivar have shown neither susceptibility nor resistance to typical pests of *Leucothoe*.

Drought Tolerance: None.

Temperature Tolerance: USDA Zones 5 through 9.

What is claimed is:

1. A new and distinct cultivar of *Leucothoe* plant named 'BLLE01' as herein illustrated and described.

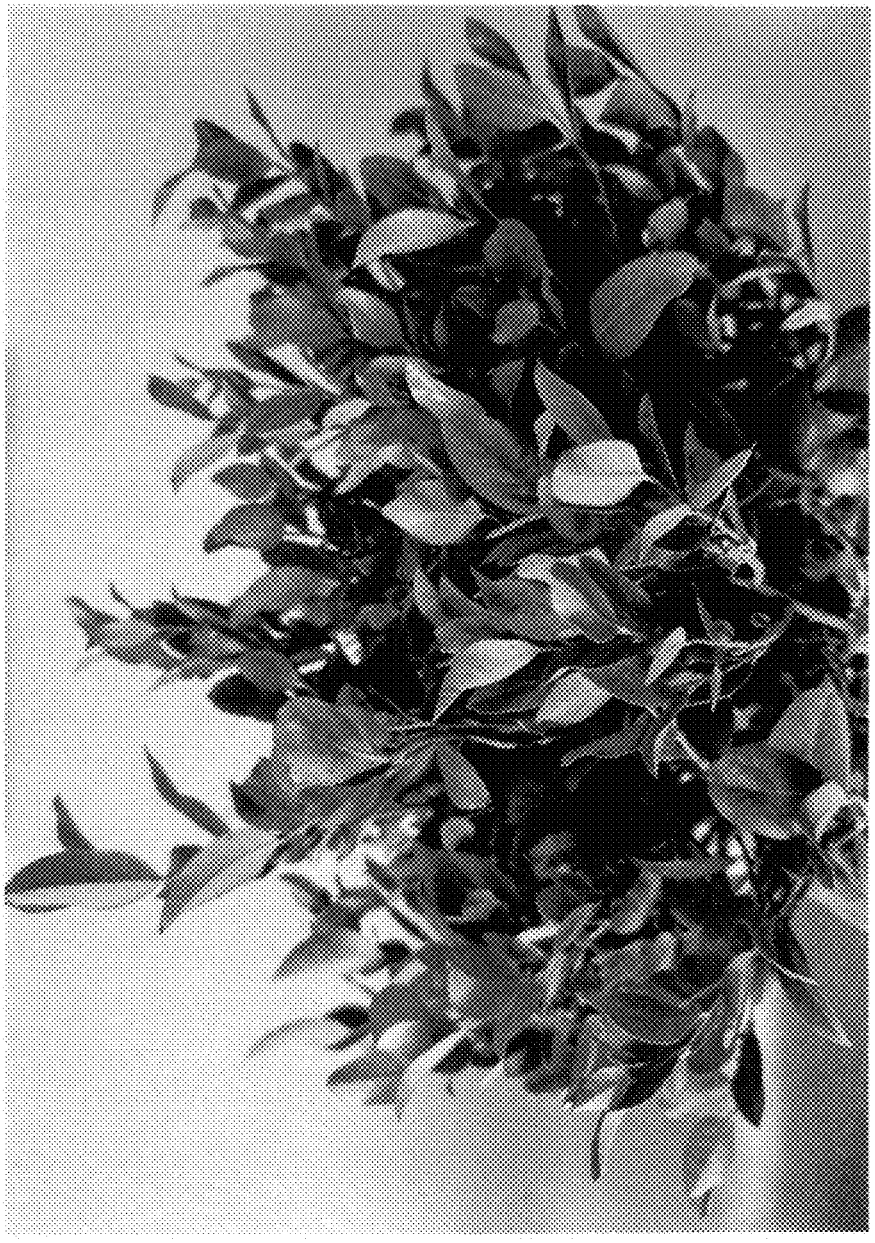

* * * * *